US008940878B2

(12) United States Patent
Shultz et al.

(10) Patent No.: US 8,940,878 B2
(45) Date of Patent: *Jan. 27, 2015

(54) CAPTURE PURIFICATION PROCESSES FOR PROTEINS EXPRESSED IN A NON-MAMMALIAN SYSTEM

(75) Inventors: Joseph Edward Shultz, Santa Rosa Valley, CA (US); Roger Hart, Loveland, CO (US)

(73) Assignee: Amgen Inc., Thousand Oaks, CA (US)

( * ) Notice: Subject to any disclaimer, the term of this patent is extended or adjusted under 35 U.S.C. 154(b) by 471 days.

This patent is subject to a terminal disclaimer.

(21) Appl. No.: 12/822,990

(22) Filed: Jun. 24, 2010

(65) Prior Publication Data

US 2010/0331526 A1    Dec. 30, 2010

Related U.S. Application Data

(60) Provisional application No. 61/220,477, filed on Jun. 25, 2009.

(51) Int. Cl.
| | | |
|---|---|---|
| *C07K 1/22* | (2006.01) | |
| *C07K 1/14* | (2006.01) | |
| *C07K 1/18* | (2006.01) | |
| *C07K 1/32* | (2006.01) | |

(52) U.S. Cl.
CPC . *C07K 1/22* (2013.01); *C07K 1/145* (2013.01); *C07K 1/18* (2013.01); *C07K 1/32* (2013.01)
USPC ............................................. 530/413

(58) Field of Classification Search
CPC .............. C07K 1/22; C07K 1/18; C07K 1/32; C07K 1/145
See application file for complete search history.

(56) References Cited

U.S. PATENT DOCUMENTS

| 5,466,377 A | 11/1995 | Grandics et al. | |
|---|---|---|---|
| 6,660,843 B1 | 12/2003 | Feige et al. | |
| 6,972,327 B1 * | 12/2005 | Madani et al. | 530/413 |
| 7,138,370 B2 | 11/2006 | Oliner et al. | |
| 7,511,012 B2 | 3/2009 | Han et al. | |

FOREIGN PATENT DOCUMENTS

| WO | WO97/28272 | 8/1997 |
|---|---|---|
| WO | WO2009/023270 | 2/2009 |

OTHER PUBLICATIONS

Pavlinkova et al. (Nuclear Med. Biol., 26:27-34, 1999).*
Ronnmark et al. (J. Immunologic. Meth., 261:199-211, 2002).*
Tengliden (Development of Cleaning-In-Place Procedures for Protein a Chromatography Resins Using Design of Experiments and High Throughput Screening Technologies, Masters Thesis, Linkoping University, Feb. 2008).*
Amersham Biosciences (Amersham Biosciences Sepharose instructions, Edition AE, p. 1-12, 2002).*
Arvidsson, P. et al., "Direct chromatographic capture of enzyme from crude homogenate using immobilized metal affinity chromatography on a continuous supermacroporous adsorbent," J. Chromatography 986 (2): 276-290 (2003).
Ling et al., "Integration of mechanical cell disruption and fluidised bed recovery of G3PHD from unclarified disrupted yeast: a comparative study of the performance of unshielded and polymer shielded dye-ligand chromatography systems," J. Biotech. 119(4): 436-448 (2005).
Fischer, B. et al., "Isolation renaturation and formation of disulfide bonds of eukaryotic proteins expressed in *escherichia coli* as inclusion bodies," Biotech. and Bioengineering, 41(1): 3-13 (1993).
Ford et al., "Affinity purification of novel bispecific antibodies recognising carcinoembryonic antigen and doxorubicin," J. Chromatogr. B, 754: 427-435 (2001).
Shukla et al., "Downstream processing of monoclonal antibodies—Application of platform approaches," Journal of Chromatography B, 848(1):28-39 (2007).
Wang et al., "Perturbation of the antigen-binding site and staphylococcal protein A-binding site of IgG before significant changes in global conformation during denaturation: an equilibrium study," Biochem. J. 325(Part 3):707-710 (1997).
Hasemann & Capra, "Immunoglobulins: Structure and Function," in William E. Paul, ed., Fundamental Immunology, Second Edition, 209, 210-218 (1989).
Ostrove, "Affinity Chromatography: General Methods," Guide to Protein Purification, Methods in Enzymology 182: 371-379 (1990).
Devereux et al., "A comprehensive set of sequence analysis programs for the VAX," Nucleosides, nucleotides; & nucleic acids: Nucl. Acids Res. 12: 387-389 (1984).
Gribskov and Burgess, "Sigma factors from *E. coli, B. subtilis*; phage SP01, and phage T4 are homologous proteins," Nucl. Acids Res. 14: 6745 (1986).
Gulich, Susanne, et al., "Protein engineering of an IgG-binding domain allows milder elution conditions during affinity chromatography," J. Biol. 76, Issues 2-3, pp. 233-244 (2000).
Ostrove "Affinity Chromatography: General Methods," Guide to Protein Purification, Methods in Enzymology 182: 357-371 (1990).
Stoscheck, C., "Quantitation of Protein," Guide to Protein Purification, Methods in Enzymology 182: 50-68 (1990).
Vola et al., "Recombinant proteins L and LG. Two new tools for purification of murine antibody fragments," Cell Biophys. 24-25: 27-36 (1994).
Aybay and Imir "Development of a rapid, single-step procedure using protein G affinity chromatography to deplete fetal calf serum of its IgG and to isolate murine IgG1 monoclonal antibodies from supernatants of hybridoma cells," Int'l. J. Immunol. Methods 233(1-2): 77-81 (2000).
Ejima, Daisuke, et al., Effective elution of antibodies by arginine and arginine derivatives in affinity column chromatography, Analytical Biochem. 345 250-257 (2005).

(Continued)

*Primary Examiner* — Brian J Gangle
(74) *Attorney, Agent, or Firm* — David B. Ran

(57) ABSTRACT

Methods of purifying proteins expressed in non-mammalian expression systems in a non-native soluble form directly from cell lysate are disclosed. Methods of purifying proteins expressed in non-mammalian expression systems in a non-native limited solubility form directly from a refold solution are also disclosed. Resin regeneration methods are also provided.

25 Claims, 5 Drawing Sheets

(56) References Cited

OTHER PUBLICATIONS

Arakawa, Tsutomu et al., "Elution of antibodies from a Protein-A column by acqueous arginine solutions," Protein Express & Purif., 36: 244-248 (2004).

Miller, Timothy et al., The rapid isolation of ribonuclease-free immunoglobulin G by protein A-sepharose affinity chromatography, J. Immun. Methods 24: 111-125 (1978).

Snyder et al., "Characterization of DC-SIGN/R Interaction with Human Immunodeficiency Virus Type 1 gp 120 and ICAM Molecules favors the receptor's role as an antigen-capturing rather than an adhesion receptor," *J. Virology* 79(8): 4589-4598, Apr. 2005.

GE Healthcare Instructions 71-7089-00AE: Affinity media, Protein A Sepharose CL-4B, p. 1-8, Mar. 2006. (Cited in JP Office action as D5 http://eclub.biomart.cn/sites/eclub.biomart.cn/themes/aktaclub/Files/71708900AE_UM_Protein_A_Sepharose_CL-4B.pdf, Mar. 2006).

GE Healthcare Instructions 71-5002-60 AE: Ion exchange chromatography; Q Sepharose XL, XL virus licensed, SP Sepharose XL, pp. 1-16, Feb. 2006 (cited in JP Office action as D6https://www.gelifesciences.com/gchels_images/GELS/Related%20Content/Files/1314723116657/litdoc71500260AE_20110830185637.pdf, Feb. 2006).

* cited by examiner

| | | Average Purity | | | | |
|---|---|---|---|---|---|---|
| | | RP-HPLC Main Peak Purity (%) | SE-HPLC Main Peak Purity (%) | CE-SDS Main Peak Purity (%) | Host Protein Level (ppm) | DNA Level (pg/mg protein) | Average Yield (%) |
| Load | Average (n=13) | 34.5 | 74.5 | 79.2 | 9100.0 | >70000 | - |
| | Std. Dev (n=13) | 2.4 | 2.7 | 4.4 | 424.3 | * | - |
| Purified Pool | Average (n=17) | 41.3 | 68.8 | 84.7 | 41.0 | 215.2 | 81.7 |
| | Std. Dev (n=17) | 1.5 | 3.8 | 4.0 | 5.7 | 301.2 | 12.3 |

* Data limited to N=1

Figure 2

|  | | Average Purity | | | | | |
|---|---|---|---|---|---|---|---|
|  | | RP-HPLC Main Peak Purity (%) | SE-HPLC Main Peak Purity (%) | CE-SDS Main Peak Purity (%) | Host Protein Level (ppm) | DNA Level (pg/mg protein) | Average Yield (%) |
| Load | Average (n=5) | 36.0 | 76.1 | 75.5 | 1400.0 | >70000 | - |
|  | Std. Dev (n=5) | 0.9 | 1.9 | 1.5 | * | * | - |
| Purified Pool | Average (150 cycles) | 40.2 | 75.0 | 82.4 | 71.4 | 89.2 | 84.3 |
|  | Std. Dev (150 cycles) | 2.5 | 8.7 | 4.6 | 23.0 | 175.0 | 18.8 |

* Data limited to N=1

Figure 3

| | RP-HPLC Main Peak Purity (%) | SE-HPLC Main Peak Purity (%) | Average Yield (%) |
|---|---|---|---|
| Load | 29.8 | 64.6 | - |
| CEX | 46.0 | 80.3 | 62.0 |
| AEX | 30.9 | 75.7 | 85.0 |

Figure 5

CAPTURE PURIFICATION PROCESSES FOR PROTEINS EXPRESSED IN A NON-MAMMALIAN SYSTEM

This application claims the benefit of U.S. Provisional Application No. 61/220,477 filed Jun. 25, 2009, which is incorporated by reference herein.

FIELD OF THE INVENTION

The present invention relates generally to processes for purifying proteins expressed in non-mammalian systems in both non-native soluble and non-native insoluble forms, and more particularly to the direct capture of such proteins from a refold mixture or a cell lysate pool by a separation matrix.

BACKGROUND OF THE INVENTION

Fc-containing proteins are typically expressed in mammalian cells, such as CHO cells. The use of affinity chromatography to purify Fc-containing proteins is documented (see, e.g., Shukla et al., (2007) *Journal of Chromatography B* 848 (1):28-39) and is successful, in part, due to the degree of Fc structure observed in proteins expressed in such systems. Fc-containing proteins expressed in non-mammalian cells, however, are often deposited in the expressing cells in limited solubility forms, such as inclusion bodies, that require refolding, and this has been a limiting factor in selecting non-mammalian systems for expressing Fc-containing proteins.

A drawback to the use of Protein A, Protein G and other chemistries is that in order for a protein comprising an Fc region to associate with the Protein A or Protein G molecule, the protein needs to have a minimum amount of structure. Often, the requisite amount of structure is absent from proteins expressed recombinantly in a soluble, but non-native, form and consequently Protein A chromatography is not performed in a purification process.

In the case of a protein expressed in an insoluble non-native form, Protein A chromatography is typically not performed in a purification process until after the protein has been refolded to a degree that it can associate with the Protein A molecule and has been subsequently diluted out of its refold solution. This is because it was believed that after a protein has been refolded it was necessary to dilute or remove the components of the refold mixture in a wash step, due to the tendency of the components that typically make up a refold solution to disrupt interactions between the target protein and the Protein A molecules (Wang et al., (1997). *Biochem. J.* 325 (Part 3):707-710). This dilution step can consume time and resources which, when working at a manufacturing scale of thousands of liters of culture, can be costly.

The present disclosure addresses these issues by providing simplified methods of purifying proteins comprising Fc regions that are expressed in non-mammalian expression systems in a non-native soluble form or in a non-native insoluble form.

SUMMARY OF THE INVENTION

A method of purifying a protein expressed in a non-native soluble form in a non-mammalian expression system is provided. In one embodiment the method comprises (a) lysing a non-mammalian cell in which the protein is expressed in a non-native soluble form to generate a cell lysate; (b) contacting the cell lysate with an separation matrix under conditions suitable for the protein to associate with the separation matrix; (c) washing the separation matrix; and (d) eluting the protein from the separation matrix.

The protein can be a complex protein, such as a protein is selected from the group consisting of a multimeric protein, an antibody and an Fc fusion protein. The non-mammalian expression system can comprise bacteria or yeast cells. The separation matrix can be an affinity resin, such as an affinity resin selected from the group consisting of Protein A, Protein G and a synthetic mimetic affinity resin, or it can be a non-affinity resin, such as a non-affinity resin selected from the group consisting of ion exchange, mixed mode, and a hydrophobic interaction resin. The cell lysate can be filtered before it is contacted with the separation matrix. Although not required, the method can further comprise refolding the protein to its native form after it is eluted from the separation matrix.

A method of purifying a protein expressed in a non-native limited solubility form in a non-mammalian expression system is provided. In one embodiment that method comprises (a) expressing a protein in a non-native limited solubility form in a non-mammalian cell; (b) lysing a non-mammalian cell; (c) solubilizing the expressed protein in a solubilization solution comprising one or more of the following: (i) a denaturant; (ii) a reductant; and (iii) a surfactant; (d) forming a refold solution comprising the solubilization solution and a refold buffer, the refold buffer comprising one or more of the following: (i) a denaturant; (ii) an aggregation suppressor; (iii) a protein stabilizer; and (iv) a redox component; (e) applying the refold solution to a separation matrix under conditions suitable for the protein to associate with the matrix; (f) washing the separation matrix; and (g) eluting the protein from the separation matrix.

The non-native limited solubility form can be a component of an inclusion body. The protein can be a complex protein, such as a complex protein selected from the group consisting of a multimeric protein, an antibody, a peptibody, and an Fc fusion protein. The non-mammalian expression system can be bacteria or yeast cells. The denaturant can comprise one or more of urea, guanidinium salts, dimethyl urea, methylurea and ethylurea, the reductant can comprise one or more of cysteine, DTT, beta-mercaptoethanol and glutathione, the surfactant can comprise one or more of sarcosyl and sodium dodecylsulfate, the aggregation suppressor can be selected from the group consisting of arginine, proline, polyethylene glycols, non-ionic surfactants, ionic surfactants, polyhydric alcohols, glycerol, sucrose, sorbitol, glucose, tris, sodium sulfate, potassium sulfate and osmolytes, the protein stabilizer can comprise one or more of arginine, proline, polyethylene glycols, non-ionic surfactants, ionic surfactants, polyhydric alcohols, glycerol, sucrose, sorbitol, glucose, tris, sodium sulfate, potassium sulfate and osmolytes, and the redox component can comprise one or more of glutathione-reduced, glutathione-oxidized, cysteine, cystine, cysteamine, cystamine and beta-mercaptoethanol. The separation matrix can be an affinity resin such as an affinity resin selected from the group consisting of Protein A, Protein G, and synthetic mimetic affinity resin or the separation matrix can be a non-affinity resin selected from the group consisting of ion exchange, mixed mode, and a hydrophobic interaction resin.

In other embodiments, the disclosed methods can further comprise the steps of (a) washing the separation matrix with a regeneration reagent; and (b) regenerating the separation matrix. The regeneration reagent can be one of a strong base, such as sodium hydroxide or a strong acid, such as phosphoric acid. The regenerating can comprise washing the separation matrix with a solution comprising one or both of a chaotrope present at a concentration of 4-6 M and a reductant. The chaotrope can be one of urea, dimethyl urea, methylurea, ethylurea, and guanidinium, and the reductant can be one of cysteine, DTT, beta-mercaptoethanol and glutathione. In a particular embodiment the regenerating comprises washing the separation matrix with a solution comprising 50 mM Tris, 10 mM citrate, 6M urea, 50 mM DTT at pH 7.4.

BRIEF DESCRIPTION OF THE DRAWINGS

FIG. 2 is a table demonstrating purification of a complex protein comprising an Fc domain using Protein A resin.

FIG. 3 is a table demonstrating the reusability of Protein A resin when used to capture a non-mammalian non-native limited solubility complex protein over 150 cycles using the disclosed methods.

FIG. 5 is a table demonstrating purification levels achieved for a protein comprising an Fc domain using one anion exhange resin (Fractogel TMAE™) and one cation exchange resin (Fractogel $SO_3^-$™).

DETAILED DESCRIPTION OF THE INVENTION

Figure 1:
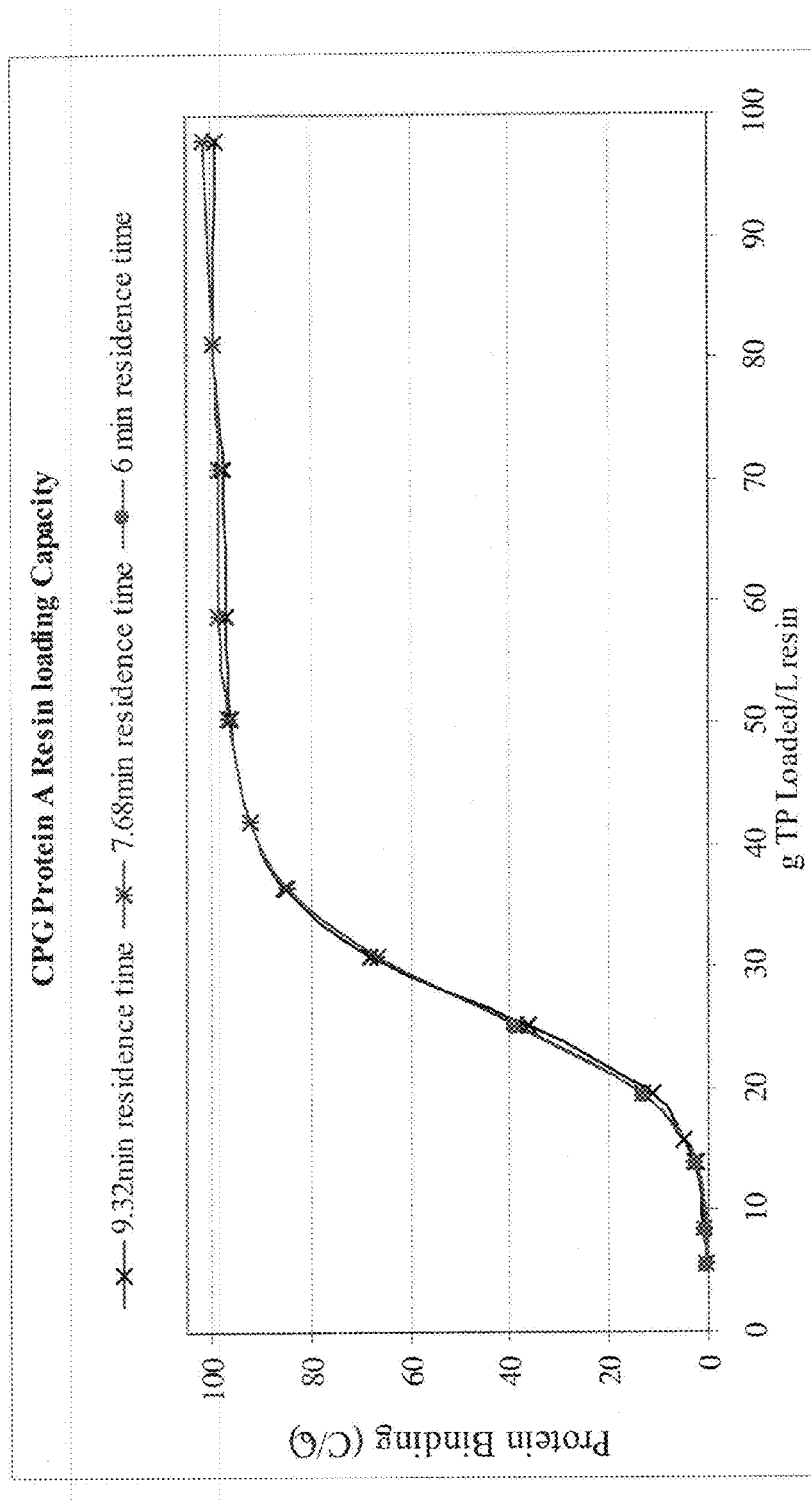
FIG. 1 is a plot demonstrating the binding of refolded, non-mammalian non-native limited solubility fraction complex protein, to Protein A media; in the figure the X denotes resin loading at a 9.32 min residence time, star denotes resin loading at a 7.68 min residence time and solid circles denote resin loading at a 6 min residence time.
Figure 4:
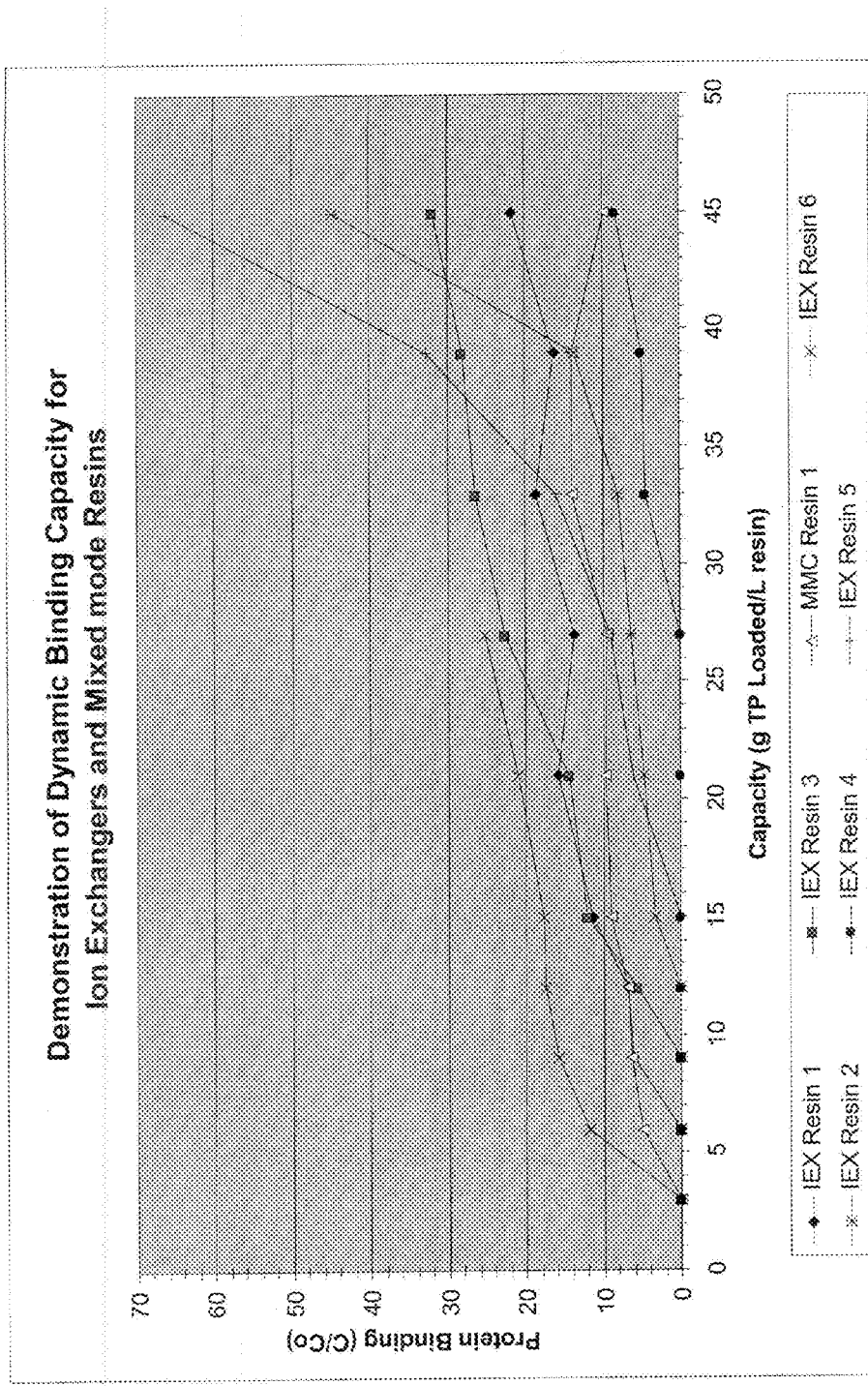
FIG. 4 is a plot demonstrating the binding profiles of a refolded, non-mammalian non-native limited solubility complex protein to six different ion exchange resins (IEX Resins 1, 2, 3, 4, 5, 6, corresponding to Toyopearl SP550C™, Toyopearl SP650M™, GigaCAP S™, POROS HS50™, Toyopearl SP650C™ and GE Healthcare SPxL™, respectively) and a mixed-mode resin (MMC Resin 1, GE Healthcare MMC™) following capture using the disclosed methods.

The present disclosure provides methods of capturing on a separation matrix non-native proteins produced in microbial cells. In the case of the direct capture of a protein expressed in a non-native soluble form the advantages of the present invention over typical processes include enhanced protein concentration, volume reduction, and increased recovery over traditional methods, improved protein stability, and ultimately process cost savings.

In the case of the direct capture of a protein expressed in a non-native limited solubility form, the advantages of the present invention over typical processes include the elimination of the need to dilute the protein out of a refold solution prior to capturing it on a separation matrix.

Another advantage of the disclosed methods is that they may be performed at a range of scales, from laboratory scale (typically milliliter or liter scale), a pilot plant scale (typically hundreds of liters) or on an industrial scale (typically thousands of liters). The application of the disclosed methods on large scales may be particularly desirable, due to the potential savings in time and resources.

Non-mammalian, e.g., microbial, cells can naturally produce, or can be engineered to produce, proteins that are expressed in either a soluble or a limited solubility form. Most often, engineered non-mammalian cells will deposit the recombinant proteins into large limited solubility aggregates called inclusion bodies. However, certain cell growth conditions (e.g., temperature or pH) can be modified to drive the recombinant proteins to be expressed as intracellular, soluble monomers. As an alternative to producing a protein of interest in cells in which the protein is expressed in the form of limited solubility inclusion bodies, cell growth conditions can be modified such that proteins are expressed in a non-native yet soluble form. The cells can then be lysed and the protein can be isolated by capturing it directly from cell lysate using ion exchange chromatography, affinity chromatography or mixed mode chromatography, as described herein. The method can be particularly useful for purifying proteins comprising an Fc region.

In one aspect, therefore, the present disclosure relates to a method of isolating a protein of interest comprising an Fc region that is expressed in a non-mammalian cell in a non-native, yet soluble form, from a pool of lysate generated from the cell in which the protein was expressed. The method employs a separation matrix, such as Protein A. One beneficial aspect of the disclosed method is that it eliminates the need for a refolding step before the protein is applied to the separation matrix. That is, non-mammalian cells expressing the protein of interest in a non-native soluble form can be lysed, the lysate applied directly to the separation matrix and the protein subsequently eluted from the separation matrix. This process allows the separation of proteins from cell cultures in highly concentrated pools that can be subsequently refolded at high concentrations and can be of benefit when producing large quantities of protein, particularly since the method is scalable from bench scale, which involves cultures on the order of several liters, up to production scale, which involves cultures of thousands of liters.

Following isolation by the separation matrix, the protein of interest can optionally be subsequently refolded using any technique known or suspected to work well for the protein of interest.

In another aspect, the present invention relates to a method of isolating a protein of interest comprising an Fc region that is expressed in a non-native limited solubility form, for example in inclusion bodies, that needs to be refolded and isolated from the refold mixture. Commonly, a refold solution contains a denaturant (e.g., urea or other chaotrope, organic solvent or strong detergent), an aggregation suppressor (e.g., a mild detergent, arginine or low concentrations of PEG), a protein stabilizer (e.g., glycerol, sucrose or other osmolyte, salts) and/or a redox component (e.g., cysteine, cystine, cystamine, cysteamine, glutathione). While often beneficial for refolding proteins, these components can inhibit purification (see, e.g., Wang et al., (1997) *Biochemical Journal* 325 (Part 3):707-710) and it is necessary to isolate or dilute the protein from these components for further processing, particularly before applying the protein to a separation matrix.

In one embodiment of the disclosed method, purification is achieved by directly applying a protein of interest, which is present in a refold mixture, to a separation matrix. In this approach, following a refold step the entire refold mixture, including the protein of interest, is applied directly to a separation matrix, such as a Protein A or G resin. The protein of interest associates with the matrix in the presence of the components of refold buffer, impurities are washed away and the protein is eluted. Since the method omits the need for removing any components of the refold mixture before the refold mixture is applied to a separation matrix, the method can have the effect of saving steps, time and resources that are typically expended on removing the protein from refolding and dilution buffers in purification processes. In some cases, the method can also reduce or eliminate the need for subsequent purification steps.

The disclosed methods can also be employed to purify proteins expressed in a non-native soluble and non-native limited solubility forms in a non-mammalian expression system that have subsequently been derivatized. For example, following expression a protein comprising an Fc region can be associated with a small molecule, such as a toxin. Such conjugates can be purified using the methods described herein.

I. DEFINITIONS

As used herein, the terms "a" and "an" mean one or more unless specifically indicated otherwise.

As used herein, the term "non-mammalian expression system" means a system for expressing proteins in cells derived from an organism other than a mammal, including but not limited to, prokaryotes, including bacteria such as *E. coli*, and yeast. Often a non-mammalian expression system is employed to express a recombinant protein of interest, while in other instances a protein of interest is an endogenous protein that is expressed by a non-mammalian cell. For purposes of the present disclosure, regardless of whether a protein of interest is endogenous or recombinant, if the protein is expressed in a non-mammalian cell then that cell is a "non-mammalian expression system." Similarly, a "non-mammalian cell" is a cell derived from an organism other than a mammal, examples of which include bacteria or yeast.

As used herein, the term "denaturant" means any compound having the ability to remove some or all of a protein's secondary and tertiary structure when placed in contact with the protein. The term denaturant refers to particular chemical compounds that affect denaturation, as well as solutions comprising a particular compound that affect denaturation. Examples of denaturants that can be employed in the disclosed method include, but are not limited to urea, guanidinium salts, dimethyl urea, methylurea, ethylurea and combinations thereof.

As used herein, the term "aggregation suppressor" means any compound having the ability to disrupt and decrease or eliminate interactions between two or more proteins. Examples of aggregation suppressors can include, but are not limited to, amino acids such as arginine, proline, and glycine; polyols and sugars such as glycerol, sorbitol, sucrose, and trehalose; surfactants such as, polysorbate-20, CHAPS, Triton X-100, and dodecyl maltoside; and combinations thereof.

As used herein, the term "protein stabilizer" means any compound having the ability to change a protein's reaction equilibrium state, such that the native state of the protein is improved or favored. Examples of protein stabilizers can include, but are not limited to, sugars and polyhedric alcohols such as glycerol or sorbitol; polymers such as polyethylene glycol (PEG) and α-cyclodextrin; amino acids salts such as arginine, proline, and glycine; osmolytes and certain Hoffmeister salts such as Tris, sodium sulfate and potassium sulfate; and combinations thereof.

As used herein, the terms "Fc" and "Fc region" are used interchangeably and mean a fragment of an antibody that comprises human or non-human (e.g., murine) $C_{H2}$ and $C_{H3}$ immunoglobulin domains, or which comprises two contiguous regions which are at least 90% identical to human or non-human $C_{H2}$ and $C_{H3}$ immunoglobulin domains. An Fc can but need not have the ability to interact with an Fc receptor. See, e.g., Hasemann & Capra, "Immunoglobulins: Structure and Function," in William E. Paul, ed., *Fundamental Immunology*, Second Edition, 209, 210-218 (1989), which is incorporated by reference herein in its entirety.

As used herein, the terms "protein" and "polypeptide" are used interchangeably and mean any chain of at least five naturally or non-naturally occurring amino acids linked by peptide bonds.

As used herein, the term "complex molecule" means any protein that is (a) larger than 20,000 MW, or comprises greater than 250 amino acid residues, and (b) comprises two or more disulfide bonds in its native form. A complex molecule can, but need not, form multimers. Examples of complex molecules include but are not limited to, antibodies, peptibodies and polypeptides comprising an Fc domain and other large proteins. Peptibodies are described in U.S. Pat. No. 6,660,843, U.S. Pat. No. 7,138,370 and U.S. Pat. No. 7,511,012.

As used herein, the term "peptibody" refers to a polypeptide comprising one or more bioactive peptides joined together, optionally via linkers, with an Fc domain. See U.S. Pat. No. 6,660,843, U.S. Pat. No. 7,138,370 and U.S. Pat. No. 7,511,012 for examples of peptibodies.

As used herein, the terms "Fc fusion" and "Fc fusion protein" are used interchangeably and refer to a peptide or polypeptide covalently attached to an Fc domain.

As used herein the term "Protein A" means any protein identical or substantially similar to Staphylococcal Protein A, including commercially available and/or recombinant forms of Protein A. For the purposes of this invention, Protein A specifically includes engineered Protein A derived media, such as Mab Select SuRe™ media (GE Healthcare), in which a single subunit (e.g., the B subunit) is replicated two or more times and joined in a contiguous sequence to form a recombinant Protein A molecule, and other non-naturally occurring Protein A molecules.

As used herein, the term "Protein G" means any protein identical or substantially similar to Streptococcal Protein G, including commercially available and/or recombinant forms of Protein G.

As used herein, the term "substantially similar," when used in the context of a protein, including Protein A, means proteins that are at least 80%, preferably at least 90% identical to each other in amino acid sequence and maintain or alter in a desirable manner the biological activity of the unaltered protein. Included in amino acids considered identical for the purpose of determining whether proteins are substantially similar are amino acids that are conservative substitutions, unlikely to affect biological activity, including the following: Ala for Ser, Val for Ile, Asp for Glu, Thr for Ser, Ala for Gly, Ala for Thr, Ser for Asn, Ala for Val, Ser for Gly, Tyr for Phe, Ala for Pro, Lys for Arg, Asp for Asn, Leu for Ile, Leu for Val, Ala for Glu, Asp for Gly, and these changes in the reverse. See, e.g., Neurath et al., *The Proteins*, Academic Press, New York (1979). The percent identity of two amino sequences can be determined by visual inspection and mathematical calculation, or more preferably, the comparison is done by comparing sequence information using a computer program such as the Genetics Computer Group (GCG; Madison, Wis.) Wisconsin package version 10.0 program, "GAP" (Devereux et al., 1984, *Nucl. Acids Res.* 12: 387) or other comparable computer programs. The preferred default parameters for the "GAP" program includes: (1) the weighted amino acid comparison matrix of Gribskov and Burgess ((1986), *Nucl. Acids Res.* 14: 6745), as described by Schwartz and Dayhoff, eds., *Atlas of Polypeptide Sequence and Structure*, National Biomedical Research Foundation, pp. 353-358 (1979), or other comparable comparison matrices; (2) a penalty of 30 for each gap and an additional penalty of 1 for each symbol in each gap for amino acid sequences; (3) no penalty for end gaps; and (4) no maximum penalty for long gaps. Other programs used by those skilled in the art of sequence comparison can also be used.

As used herein, the terms "isolate" and "purify" are used interchangeably and mean to reduce by 1%, 2%, 3%, 4%, 5%, 10%, 15%, 20%, 25%, 30%, 35%, 40%, 45%, 50%, 55%, 60%, 65%, 70%, 75%, 80%, 85%, 90% or 95%, or more, the amount of heterogenous elements, for example biological macromolecules such as proteins or DNA, that may be present in a sample comprising a protein of interest. The presence of heterogenous proteins can be assayed by any appropriate method including High-performance Liquid Chromatography (HPLC), gel electrophoresis and staining and/or ELISA assay. The presence of DNA and other nucleic acids can be assayed by any appropriate method including gel electrophoresis and staining and/or assays employing polymerase chain reaction.

As used herein, the term "separation matrix" means any adsorbent material that utilizes specific, reversible interactions between synthetic and/or biomolecules, e.g., the property of Protein A to bind to an Fc region of an IgG antibody or other Fc-containing protein, in order to effect the separation of the protein from its environment. In other embodiments the specific, reversible interactions can be base on a property such as isoelectric point, hydrophobicity, or size. In one particular embodiment, a separation matrix comprises an adsorbent, such as Protein A, affixed to a solid support. See, e.g., Ostrove (1990) in "Guide to Protein Purification," *Methods in Enzymology* 182: 357-379, which is incorporated herein in its entirety.

As used herein, the terms "non-native" and "non-native form" are used interchangeably and when used in the context of a protein of interest, such as a protein comprising a Fc domain, mean that the protein lacks at least one formed structure attribute found in a form of the protein that is biologically active in an appropriate in vivo or in vitro assay designed to assess the protein's biological activity. Examples of structural features that can be lacking in a non-native form of a protein can include, but are not limited to, a disulfide bond, quaternary structure, disrupted secondary or tertiary structure or a state that makes the protein biologically inactive in an appropriate assay. A protein in a non-native form can but need not form aggregates.

As used herein, the term "non-native soluble form" when used in the context of a protein of interest, such as a protein comprising a Fc domain, means that the protein lacks at least one formed structure attribute found in a form of the protein that is biologically active in an appropriate in vivo or in vitro assay designed to assess the protein's biological activity, but in which the protein is expressed in a form or state that is soluble intracellularly (for example in the cell's cytoplasm) or extracellularly (for example, in a lysate pool).

As used herein, the term "non-native limited solubility form" when used in the context of a protein of interest, such as a protein comprising a Fc domain, means any form or state in which the protein lacks at least one formed structural feature found in a form of the protein that (a) is biologically active in an appropriate in vivo or in vitro assay designed to assess the protein's biological activity and/or (b) forms aggregates that require treatment, such as chemical treatment, to become soluble. The term specifically includes proteins existing in inclusion bodies, such as those sometimes found when a recombinant protein is expressed in a non-mammalian expression system.

As used herein, the term "soluble form" when used in the context of a protein of interest, such as a protein comprising a Fc domain, broadly refers to a form or state in which the protein is expressed in a form that is soluble in a intracellularly (for example in the cell's cytoplasm) or extracellularly (for example, in a cell lysate pool).

II. DIRECT CAPTURE OF A PROTEIN EXPRESSED IN A NON-NATIVE SOLUBLE FORM IN A NON-MAMMALIAN EXPRESSION SYSTEM

One advantage of the disclosed method over typical purification methods is the elimination of the need for a refolding step before the soluble protein is applied to the separation matrix. That is, a protein solublized in cell lysate can be directly applied to the separation matrix. This is advantageous because the method does not require any initial purification efforts, although an initial filtration step may be desirable in some cases.

In the case of a protein comprising a Fc domain, the Fc region must have a certain level of structure to be bound by protein A, (Wang et al., (1997) *Biochem. J.* 325 (Part 3):707-710). This fact has limited the application of separation matrices for purifying proteins that are expressed in a non-native soluble form, particularly proteins comprising an Fc region, because it is commonly believed that a soluble non-native Fc-containing protein would not have the requisite structural elements required to associate with a separation matrix. Furthermore, the Fc region of an antibody spontaneously forms a homodimer under non-reducing conditions and prior to the instant disclosure it was unexpected to observe that even in the reductive environment of the cell, the Fc-conjugated proteins and peptides not only form enough structure for protein to bind to the affinity resin, but that the individual peptide chains readily formed non-covalent dimers, even though the proteins had not yet been completely refolded to native form.

In view of prevailing beliefs, the success of the disclosed method was surprising and unanticipated because it was not expected that a non-mammalian, microbial cell fermentation could be induced to produce a protein that was soluble, yet still had enough structure to associate with the affinity separation matrix.

The disclosed method can be employed to purify a protein of interest that is expressed in a non-native soluble form in a non-mammalian cell expression system. The protein of interest can be produced by living host cells that either naturally produce the protein or that have been genetically engineered to produce the protein. Methods of genetically engineering cells to produce proteins are known in the art. See, e.g., Ausabel et al., eds. (1990), *Current Protocols in Molecular Biology* (Wiley, New York). Such methods include introducing nucleic acids that encode and allow expression of the protein into living host cells. In the context of the present disclosure, a host cell will be a non-mammalian cell, such as bacterial cells, fungal cells, yeast cells, and insect cells. Bacterial host cells include, but are not limited to, *Escherichia coli* cells. Examples of suitable *E. coli* strains include: HB101, DH5α, GM2929, JM109, KW251, NM538, NM539, and any *E. coli* strain that fails to cleave foreign DNA. Fungal host cells that can be used include, but are not limited to, *Saccharomyces cerevisiae, Pichia pastoris* and *Aspergillus* cells. New cell lines can be established using methods known to those skilled in the art (e.g., by transformation, viral infection, and/or selection). It is noted that the method can be performed on proteins that are endogenously expressed by the non-mammalian cell as well.

During the production of a non-mammalian culture, growth conditions can be identified and employed so as to favor the production of a protein of interest in an intracellular soluble form. Such conditions can be identified by systematic empirical optimization of the culture condition parameters, such as temperature or pH. This optimization can be achieved using analysis of multifactorial matrices. For example, a matrix or series of multifactorial matrices can be evaluated to optimize temperature and pH conditions favor production of a desired species (i.e., a non-native soluble form). An optimization screen can be set up to systematically evaluate temperature and pH in a full or partial factorial matrix, with each component varied over a range of at least three temperature or pH levels with all other parameters kept constant. The protein can be expressed and the yield and quality of protein expressed in the desired form can be evaluated using standard multivariate statistical tools.

Initially, non-mammalian cells that express a particular protein of interest are grown to a desired target density under conditions designed to induce expression of the protein in a soluble form. In one embodiment, the cells express a wild type protein of interest. In another embodiment, the cells can be engineered using standard molecular biology techniques to recombinantly express a protein of interest, and induced to produce the protein of interest. The protein of interest can be any protein, for example a protein that comprises an Fc moiety. Such a protein can be, for example, an antibody, a peptibody or an Fc fusion protein, any of which can be joined to an Fc moiety via a linker.

Once the desired target density is reached, the non-mammalian cells are separated from the growth media. One convenient way of achieving separation is by centrifugation, however filtration and other clarification methods can also be used.

The cells are then collected and are resuspended to an appropriate volume in a resuspension solution. Examples of resuspension solutions that can be used in the disclosed methods include phosphate buffered saline, Tris buffered saline, or water. The selection of an appropriate buffer will be determined, in part, by the properties of the molecule of interest as well as any volume or concentration constraints.

Following resuspension, the non-mammalian cells are lysed to release the protein, which will be present in the cell lysate in a non-native soluble form to generate a cell lysate. The lysis can be performed using any convenient means, such as feeding the cell suspension through a high pressure homogenizer or by employing a chemical lysis process. Whichever lytic process is selected, the function of the lysis step is to break open the cells and to break down DNA. The lysis can be performed in multiple cycles to achieve a more complete lysis or to accommodate large volumes of cell suspension. For example, the cell suspension can be fed through a mechanical homogenizer several times. This process releases the intracellular contents, including the protein of interest, and forms a pool of cell lysate.

Following the lysis procedure, the cell lysate can optionally be filtered. Filtration can remove particulate matter and/or impurities, such as nucleic acids and lipids, and may be desirable in some cases, such as when one suspects that direct application of the cell lysate to the chromatography equipment or media may lead to fouling or clogging, or when the separation matrix is sensitive to fouling or difficult to clean in-place. The benefit of filtering the cell lysate prior to contacting it with the separation matrix can be determined on a case-by-case basis.

After the lysis procedure, the cell lysate can optionally be incubated for an appropriate amount of time in the presence of air or oxygen, or exposed to a redox component or redox thiol-pair. The incubation can facilitate and/or ensure the formation of the minimal secondary structure required to facilitate an association with a separation matrix. The particular length of the incubation can vary with the protein but is typically less than 72 hours (e.g., 0, 0.5, 1, 2, 3, 5, 7, 10, 12, 18, 24, 36, 48 or 72 hours). When an incubation is performed, the length of incubation time can be determined by empirical analysis for each protein, which in some cases will be shorter (or omitted) and other cases longer.

Following the incubation period the cell lysate, which comprises the released protein of interest, is contacted with a separation matrix under conditions suitable for the protein to associate with a binding element of the separation matrix. Representative conditions conducive to the association of a protein with an affinity matrix are provided in the Examples. The separation matrix can be any media by which the protein of interest can be separated from the components of the resuspension and/or lysis buffer, including impurities such as host cell proteins, DNA, lipids and chemical impurities introduced by the components of the resuspension and/or lysis buffer.

Proteins A and G are often employed to purify antibodies, peptibodies and other fusion proteins comprising a Fc region by affinity chromatography. See, e.g., Vola et al. (1994), *Cell Biophys.* 24-25: 27-36; Aybay and Imir (2000), *J. Immunol. Methods* 233(1-2): 77-81; Ford et al. (2001), *J. Chromatogr. B* 754: 427-435. Proteins A and G are useful in this regard because they bind to the Fc region of these types of proteins. Recombinant fusion proteins comprising an Fc region of an IgG antibody can be purified using similar methods. Proteins A and G can be employed in the disclosed methods as an adsorbent component of a separation matrix.

Thus, examples of separation matrices that can be employed in the present invention include Protein A resin, which is known to be, and is commonly employed as, an effective agent for purifying molecules comprising an Fc moiety, as well as Protein G and synthetic mimetic affinity resins, such as MEP HyperCel® chromatography resin.

After the protein of interest has been associated with the separation matrix by contacting the cell lysate containing the protein with the separation matrix, thereby allowing the protein to associate with the adsorbent component of the separation matrix, the separation matrix is washed to remove unbound lysate and impurities.

The wash buffer can be of any composition, as long as the composition and pH of the wash buffer is compatible with both the protein and the matrix, and maintains the interaction between the protein and the matrix. Examples of suitable wash buffers that can be employed include solutions containing glycine, Tris, citrate, or phosphate; typically at levels of 5-100 mM (e.g., 5, 10, 15, 20, 25, 30, 35, 40, 45, 50, 75 or 100 mM). These solutions can also contain an appropriate salt ion, such as chloride, sulfate or acetate at levels of 5-500 mM (e.g., 5, 10, 12, 30, 40, 50, 60, 70, 80, 90, 100, 150, 200, 250, 300, 350, 400, 450 or 500 mM). The resin can be washed once or any number of times. The exact composition of a wash buffer will vary with the protein being purified.

After the separation matrix with which the protein has associated has been washed, the protein of interest is eluted from the matrix using an appropriate solution. The protein of interest can be eluted using a solution that interferes with the binding of the adsorbent component of the separation matrix to the protein, for example by disrupting the interactions between the separation matrix and the protein of interest. This solution can include an agent that can either increase or decrease pH, and/or a salt. For example, the pH can be lowered to about 4.5 or less, for example to between about 3.3 and about 4.0, e.g., 3.3, 3.4, 3.5, 3.6, 3.7, 3.8, 3.9, 4.0, 4.1, 4.2, 4.3, 4.4 or 4.5. A solution comprising citrate or acetate, for example, can be employed to lower the pH. Other methods of elution are also known, such as via the use of chaotropes (see, e.g., Ejima et al. (2005) *Analytical Biochemistry* 345(2):250-257) or amino acid salts (see, e.g., Arakawa et al. (2004) *Protein Expression & Purification* 36(2):244-248). Protocols for such affinity chromatography are well known in the art. See, e.g., Miller and Stone (1978), *J. Immunol. Methods* 24(1-2): 111-125. Conditions for binding and eluting can be readily optimized by those skilled in the art. The exact composition of an elution buffer will vary with the protein being purified. The protein can then optionally be further purified from the elution pool and refolded as necessary. In other situations the protein need not be further purified and instead can be refolded directly from the elution pool. Refolding directly from the elution pool may or may not require denaturation or reduction of the protein prior to incubation in a refolding solution and will depend in part on the properties of the protein.

In some cases it will be desirable to provide the separation matrix in a column format. In such cases a chromatography column can be prepared and then equilibrated before the cell suspension is loaded. Techniques for generating a chromatography column are well known and can be employed. An optional preparation and equilibration step can comprise washing the column with a buffer having an appropriate pH and salt condition that is conducive to protein-matrix interactions. This step can provide the benefit of removing impurities present in the separation matrix and can enhance the binding of the protein to be isolated to the adsorbent component of a separation matrix.

As noted, the separation matrix can be disposed in a column. The column can be run with or without pressure and from top to bottom or bottom to top. The direction of the flow of fluid in the column can be reversed during the purification process. Purifications can also be carried out using a batch process in which the solid support is separated from the liquid used to load, wash, and elute the sample by any suitable means, including gravity, centrifugation, or filtration. Moreover, purifications can also be carried out by contacting the sample with a filter that adsorbs or retains some molecules in the sample more strongly than others, such as anion exchange membrane chromatography.

If desired, the protein concentration of a sample at any given step of the disclosed method can be determined, and any suitable method can be employed. Such methods are well known in the art and include: 1) colorimetric methods such as the Lowry assay, the Bradford assay, the Smith assay, and the colloidal gold assay; 2) methods utilizing the UV absorption properties of proteins; and 3) visual estimation based on stained protein bands on gels relying on comparison with protein standards of known quantity on the same gel. See, e.g., Stoschek (1990), "Quantitation of Protein," in "Guide to Protein Purification," *Methods in Enzymology* 182: 50-68. Periodic determinations of protein concentration can be useful for monitoring the progress of the method as it is performed.

It is noted that any or all steps of the disclosed methods can be carried out manually or by any convenient automated means, such as by employing automated or computer-controlled systems.

III. DIRECT CAPTURE OF NON-NATIVE LIMITED SOLUBILITY PROTEIN FORMS FROM A REFOLD SOLUTION FOLLOWING EXPRESSION IN NON-MAMMALIAN CELLS

In another aspect of the present disclosure, a method of purifying a protein expressed in a non-native limited solubility form in a non-mammalian expression system is disclosed. An advantage of the disclosed method is that the method eliminates the need for removing or diluting the refold solution before applying the protein to a separation matrix, thereby saving the time and resources associated with what is a typical step in a purification process for isolating proteins expressed in a non-native limited solubility form.

Non-mammalian cells, e.g., microbial cells, can produce recombinant proteins that are expressed intracellularly in either a soluble or a limited solubility form. When the growth conditions are not directed to force expression of the protein in a soluble form, the cells may deposit the recombinant proteins into large relatively insoluble aggregates, such as inclusion bodies. These aggregates comprise protein that is typically not biologically active or less active than the completely folded native form of the protein. In order to produce a functional protein, these inclusion bodies often need to be carefully denatured so that the protein of interest can be extracted and refolded into a biologically active form.

In typical approaches, the inclusion bodies need to be captured, washed, exposed to a denaturing and/or reducing solubilization solution and the denaturing solution is then diluted with a solution to generate a condition that allows the protein to refold into an active form and form a structure that is found in the native protein. Subsequently, it is necessary to remove the components of the diluted denaturing solution from the immediate location of the protein. In order to do this, the refold solution comprising the solubilization solution and the refolded protein is typically diluted with a buffered solution before it is applied to a separation matrix, such as a Protein A ion exchange or other mixed-mode adsorbents. This process can be time-consuming and resource-intensive. It also significantly increases the volumes that need to be handled, as well as the associated tankage requirements, which can become limiting when working on large scales. The disclosed method eliminates the need for such a dilution step The disclosed method is particularly useful for purifying a protein of interest that is expressed in a non-native limited solubility form in a non-mammalian cell expression system. The protein of interest can be produced by living host cells that either naturally produce the protein or that have been genetically engineered to produce the protein. Methods of genetically engineering cells to produce proteins are well known in the art. See, e.g., Ausabel et al., eds. (1990), *Current Protocols in Molecular Biology* (Wiley, New York). Such methods include introducing nucleic acids that encode and allow expression of the protein into living host cells. In the context of the present disclosure, these host cells will be non-mammalian cells, such as bacterial cells, fungal cells. Bacterial host cells include, but are not limited to *Escherichia coli* cells. Examples of suitable *E. coli* strains include: HB101, DH5α, GM2929, JM109, KW251, NM538, NM539, and any *E. coli* strain that fails to cleave foreign DNA. Fungal host cells that can be used include, but are not limited to, *Saccharomyces cerevisiae, Pichia pastoris* and *Aspergillus* cells. New cell lines can be established using methods well know by those skilled in the art (e.g., by transformation, viral infection, and/or selection). It is noted that the method can be performed on endogenous proteins that are naturally expressed by the non-mammalian cell as well.

Initially, non-mammalian cells that express a particular protein of interest are grown to a desired target density. In one embodiment, the cells can be expressing a particular wild type microbial protein of interest. In another embodiment, the cells can be engineered using standard molecular biology techniques to recombinantly express a protein of interest, and in this context they can be induced to overproduce the protein of interest. The protein of interest can be any protein, for example a protein that comprises an Fc moiety. Such a protein can be, for example, an antibody, a peptibody or an Fc fusion protein, any of which can be joined to an Fc moiety via a linker.

Once the desired target density is reached, the non-mammalian cells can be separated from the growth media. One convenient way of achieving separation is by centrifugation, however filtration and other clarification methods can also be used.

The cells are then collected and are resuspended to an appropriate volume in a resuspension solution. Examples of resuspension solutions that can be used in the present invention include phosphate-buffered saline, Tris-buffered saline, or water. The selection of an appropriate buffer will be determined, in part, by the properties of the molecule of interest as well as any volume or concentration constraints.

In order to release the limited solubility non-native protein from the cells, the non-mammalian cells are lysed to form a cell lysate comprising the released the limited solubility non-native protein. The lysis can be performed in any convenient way, such as feeding the cell suspension through a high pressure homogenizer or by employing a chemical lysis process. Whichever lysis process is selected, the function of the lysis step is to break open the cells and to break down DNA. The lysis can be performed in multiple cycles to achieve a more complete lysis or to accommodate large volumes of cell suspension. For example, the cell suspension can be fed through a mechanical homogenizer several times. This process releases the intracellular contents, including the naturally-occurring or recombinant protein of interest, and forms a pool of cell lysate.

Next, the limited solubility non-native protein is separated from the rest of the lysis pool. This can be done, for example, by centrifugation. Representative conditions for a centrifuge-mediated separation or washing typically include removal of excess water from the cell lysate, resuspension of the resulting slurry in a resuspension solution. This washing process may be performed once or multiple times. Examples of typical centrifuge types include, but are not limited to, disk-stack, continuous discharge, and tube bowl. Examples of resuspension solutions that can be used in the present invention include phosphate-buffered saline, Tris-buffered saline, or water and can include other agents, such as ETDA or other salts. The selection of an appropriate buffer will be determined, in part, by the properties of the molecule of interest as well as any volume or concentration constraints. The exact composition of an resuspension buffer will vary with the protein being purified.

The expressed protein is then solubilized in a solubilization solution comprising one or more of (i) a denaturant, (ii) a reductant and (iii) a surfactant. The denaturant can be included as a means of unfolding the limited solubility protein, thereby removing any existing structure, exposing buried residues and making the protein more soluble.

Any denaturant can be employed in the solubilization solution. Examples of some common denaturants that can be employed in the refold buffer include urea, guanidinium, dimethyl urea, methylurea, or ethylurea. The specific concentration of the denaturant can be determined by routine optimization.

The reductant can be included as a means to reduce exposed residues that have a propensity to form covalent intra or intermolecular-protein bonds and minimize non-specific bond formation. Examples of suitable reductants include, but are not limited to, cysteine, DTT, beta-mercaptoethanol and glutathione. The specific concentration of the reductant can be determined by routine optimization.

A surfactant can be included as a means of unfolding the limited solubility non-native protein, thereby exposing buried residues and making the protein more soluble. Examples of suitable surfactants include, but are not limited to, sarcosyl and sodium dodecylsulfate. The specific concentration of the surfactant can be determined by routine optimization.

Although the composition of a solubilization solution will vary with the protein being purified, in one particular embodiment the solubilization solution comprises 4-6 M guanidine, 50 mM DTT.

Continuing, a refold solution comprising the solubilization solution (which comprises the protein), and a refold buffer is formed. The refold buffer comprises one or more of (i) a denaturant; (ii) an aggregation suppressor; (iii) a protein stabilizer; and (iv) a redox component. The denaturant can be included as a means of modifying the thermodynamics of the solution, thereby shifting the equilibrium towards an optimal balance of native form. The aggregation suppressor can be included as a means of preventing non-specific association of one protein with another, or with one region of a protein with another region of the same protein. The protein stabilizer can be included as a means of promoting stable native protein structure and may also suppress aggregation.

In various embodiments, the denaturant in the refold buffer can be selected from the group consisting of urea, guanidinium salts, dimethyl urea, methylurea and ethylurea.

In various embodiments, the protein stabilizer in the refold buffer can be selected from the group consisting of arginine, proline, polyethylene glycols, non-ionic surfactants, ionic surfactants, polyhydric alcohols, glycerol, sucrose, sorbitol, glucose, Tris, sodium sulfate, potassium sulfate and osmolytes.

In various embodiments, the aggregation suppressor can be selected from the group consisting of arginine, proline, polyethylene glycols, non-ionic surfactants, ionic surfactants, polyhydric alcohols, glycerol, sucrose, sorbitol, glucose, Tris, sodium sulfate, potassium sulfate and osmolytes.

In various embodiments, the thiol-pairs can comprise at least one component selected from the group consisting of glutathione-reduced, glutathione-oxidized, cysteine, cystine, cysteamine, cystamine and beta-mercaptoethanol.

The specific concentrations of the components of a refold buffer can be determined by routine optimization. For example, a matrix or series of multifactorial matrices can be evaluated to optimize the refolding buffer for conditions that optimize yield and distributions of desired species. An optimization screen can be set up to systematically evaluate denaturant, aggregation suppressor, protein stabilizer and redox component concentrations and proportions in a full or partial factorial matrix, with each component varied over a range of concentrations with all other parameters kept constant. The completed reactions can be evaluated by RP-HPLC and SE-HPLC analysis for yield and product quality using standard multivariate statistical tools.

The function of the buffer component of the refold solution is to maintain the pH of the refold solution and can comprise any buffer that buffers in the appropriate pH range. Examples of the buffering component of a refold buffer that can be employed in the method include, but are not limited to, phosphate buffers, citrate buffers, tris buffer, glycine buffer, CHAPS, CHES, and arginine-based buffers, typically at levels of 5-100 mM (e.g., 5, 10, 15, 20, 25, 30, 35, 40, 45, 50, 55, 60, 65, 70, 75 80, 85, 90, 95 or 100, mM).

Although the composition of an refold buffer will vary with the protein being purified, in one embodiment a refold buffer comprises arginine, urea, glycerol, cysteine and cystamine.

The refold solution can then be incubated for a desired period of time. The incubation period can be of any length but is typically between 0 and 72 hours (e.g., 0, 0.5, 1, 2, 3, 5, 7, 10, 12, 18, 24, 36, 48 or 72 hours).

After an appropriate incubation time, the refold solution is then applied to a separation matrix under conditions suitable for the protein to associate with the matrix. The separation matrix can be any media by which the protein of interest can be separated from the components of the resuspension and/or lysis buffer, including impurities such as host cell proteins, DNA and chemical impurities introduced by the components of the solubilization and/or lysis buffer.

Proteins A and G are often employed to purify antibodies, peptibodies and other fusion proteins comprising a Fc region by affinity chromatography. See, e.g., Vola et al. (1994), *Cell Biophys.* 24-25: 27-36; Aybay and Imir (2000), *J. Immunol. Methods* 233(1-2): 77-81; Ford et al. (2001), *J. Chromatogr. B* 754: 427-435. Proteins A and G are useful in this regard because they bind to the Fc region of these types of proteins. Recombinant fusion proteins comprising an Fc region of an IgG antibody can be purified using similar methods. Proteins A and G can be employed in the disclosed methods as an adsorbent component of a separation matrix.

Thus, examples of affinity separation matrices that can be employed in the present invention include Protein A resin, which is know to be, and is commonly employed as, an effective agent for purifying molecules comprising an Fc moiety, as well as Protein G and synthetic mimetic affinity resins. Other materials that can be employed include HIC and ion exchange resins (see Example 4), depending on the properties of the protein to be purified.

It is noted that when performing the method, the refold solution comprising the refolded protein of interest is applied directly to the separation matrix, without the need for diluting or removing the components of the solution required for refolding the protein. This is an advantage of the disclosed method. Initially, it was expected that the highly ionic and/or chaotropic compounds and various other components of the refold solution would inhibit the association of the protein with the separation matrix. However, in contrast to reports in the literature (e.g., Wang et al. (1997) *Biochemical Journal.* 325 (Part 3):707-710), it was surprising to observe that the protein was in fact able to associate with the separation matrix in the presence of the components of the refold solution. The unexpected finding that the protein could associate with the separation matrix in the presence of the components of the refold solution facilitates the elimination of a dilution step or buffer exchange operation, providing a savings of time and resources.

After the protein of interest has associated with the separation matrix the separation matrix is washed to remove unbound protein, lysate, impurities and unwanted components of the refold solution.

The wash buffer can be of any composition, as long as the composition and pH of the wash buffer is compatible with both the protein and the matrix. Examples of suitable wash buffers that can include, but are limited to, solutions containing glycine, tris, citrate, or phosphate. These solutions may also contain an appropriate salt. Suitable salts include, but are not limited to, sodium, potassium, ammonium, magnesium, calcium, chloride, fluoride, acetate, phosphate, and/or citrate. The pH range is chosen to optimize the chromatography conditions, preserve protein binding, and to retain the desired characteristics of the protein of interest. The resin can be washed once or any number of times. The exact composition of a wash buffer will vary with the protein being purified.

After the separation matrix with which the protein has associated has been washed, the protein of interest is eluted using an appropriate solution (e.g., a low pH buffered solution or a salt solution) to form an elution pool comprising the protein of interest.

The protein of interest can be eluted using a solution that interferes with the binding of the adsorbent component of the separation matrix to the protein, for example by disrupting the interactions between Protein A and the Fc region of a protein of interest. This solution may include an agent that can either increase or decrease pH, and/or a salt. In various embodiments, the elution solution can comprise acetic acid, glycine, or citric acid. Elution can be achieved by lowering the pH. For example, the pH can be lowered to about 4.5 or less, for example to between about 3.3 to about 4.2 (e.g., 3.3, 3.4, 3.5, 3.6, 3.7, 3.8, 3.9, 4.0, 4.1 or 4.2, using a solution comprising citrate or acetate, among other possibilities.

In some situations, the protein can then be further purified from the elution pool and can be further refolded, if necessary. In other situations the protein need not be further purified and instead can be further refolded directly in the elution pool, if necessary.

Protocols for such affinity chromatography are known in the art. See, e.g., Miller and Stone (1978), *J. Immunol. Methods* 24(1-2): 111-125. In the cases that utilize ion exchange, mixed-mode, or hydrophobic interaction chromatography, the concentration of salt can be increased or decreased to disrupt ionic interaction between bound protein and a separation matrix. Solutions appropriate to effect such elutions can include, but are not limited to, sodium, potassium, ammonium, magnesium, calcium, chloride, fluoride, acetate, phosphate, and/or citrate. Other methods of elution are also known. Conditions for binding and eluting can be readily optimized by those skilled in the art.

The exact composition of an elution buffer will vary with the protein being purified and the separation matrix being employed.

In some cases it will be desirable to situate the separation matrix in a column format. In such cases a column can be prepared and then equilibrated before the cell suspension is loaded. Techniques for generating a chromatography column are well known and can be employed. The optional preparation and equilibration step can comprise washing the column with a buffer having an appropriate pH and composition that will prepare the media to bind a protein of interest. This step has the benefit of removing impurities present in the separation matrix and can enhance the binding of the protein to be isolated to the adsorbent component of a separation matrix.

It is noted that any or all steps of the invention can be carried out by any mechanical means. As noted, the separation matrix can be disposed in a column. The column can be run with or without pressure and from top to bottom or bottom to top. The direction of the flow of fluid in the column can be reversed during the purification process. Purifications can also be carried out using a batch process in which the solid support is separated from the liquid used to load, wash, and elute the sample by any suitable means, including gravity, centrifugation, or filtration. Moreover, purifications can also be carried out by contacting the sample with a filter that adsorbs or retains some molecules in the sample more strongly than others.

If desired, the protein concentration of a sample at any given step of the disclosed method can be determined by any suitable method. Such methods are well known in the art and include: 1) colorimetric methods such as the Lowry assay, the Bradford assay, the Smith assay, and the colloidal gold assay; 2) methods utilizing the UV absorption properties of proteins; and 3) visual estimation based on stained protein bands on gels relying on comparison with protein standards of known quantity on the same gel. See, e.g., Stoschek (1990), "Quantitation of Protein," in "Guide to Protein Purification," *Methods in Enzymology* 182: 50-68. Periodic determinations of protein concentration can be useful for monitoring the progress of the method as it is performed.

It is noted that any or all steps of the disclosed methods can be carried out manually or by any convenient automated means, such as by employing automated or computer-controlled systems.

IV. COLUMN CLEANING

In another aspect the present disclosure relates to the observation that in many cases the separation matrix employed in the methods provided herein can be cleaned after multiple separations and reused. This unexpected property of the method provides a significant cost and resource savings, particularly on the manufacturing scale, since the separation matrix need not be discarded after a separation is complete.

Common wisdom in the industry suggests that after a separation matrix, such as Protein A, is repeatedly exposed to highly heterogenous feedstocks comprising high lipid and host protein content it becomes irreversibly contaminated and unusable when treated with the mild regeneration solutions commonly utilized for protein-based affinity resins. The disclosed methods, however, avoid this situation and extend the usable lifetime of a separation matrix. In the context of a large scale manufacturing process this can translate into a measurable savings of time and money. Moreover, the cleaning step can be performed, as disclosed in the Examples, in-place and with no need to extract the separation matrix from a column or other matrix retaining device for cleaning, thus saving time and resources.

In one embodiment of a cleaning operation of a separation matrix, following a separation employing the disclosed method the separation matrix is washed with a regeneration reagent, such as sodium hydroxide, or an acidic reagent, such as phosphoric acid.

In one particular embodiment of a cleaning operation, Protein A is the separation matrix and a column containing Protein A resin is washed with 5 column volumes of 150 mM phosphoric acid and held for >15 minutes over the column. Following the wash with the acid, the column can be flushed with water, regenerated with 5 column volumes of 50 mM Tris, 10 mM citrate, 6M urea, 50 mM DTT; pH 7.4, subsequently washed with water, and then flushed with 3 column volumes of 150 mM phosphoric acid. This cleaning protocol has been utilized to achieve over 200 cycles of protein A resin. FIG. 3 highlights the results achievable using the disclosed cleaning methods.

EXAMPLES

The following examples demonstrate embodiments and aspects of the present invention and are not intended to be limiting.

Example 1

Direct Capture of Proteins Expressed in a Soluble Form Using Protein A Affinity Chromatography The following experiment demonstrates that a protein comprising a plurality of polypeptides joined to an Fc moiety can be separated from an *E. coli* cell lysate slurry using a Protein A affinity media.

A protein comprising a plurality of polypeptides joined to an Fc moiety was expressed in an *E. coli* fermentation induced at 30° C. and driven to express soluble-form protein product. The fermentation broth was centrifuged, the liquid fraction removed, and the cell paste was collected. The cells were resuspended in a 10 mM potassium phosphate, 5 mM EDTA; pH 6.8 buffer solution, to approximately 100% of the original volume. The cells were then lysed by means of three passes through a high pressure homogenizer. After the cells were lysed, the cell lysate was filtered through a 0.1 µm filter to reduce particulate levels. The material was then stored in a closed bottle for ~24 hours at approximately 5° C.

In a separate operation, a packed column comprising GE Healthcare Mab Select™ Protein A affinity resin was prepared and equilibrated with 5 column volumes (CV) of 10 mM Tris; pH 8.0.

An aliquot of a protein comprising an Fc moiety was sampled directly from a lysate. The protein mixture was loaded to approximately 0.02 millimoles total protein/L resin at a 6-10 minute residence time. See FIG. 1, which correlates protein bound and protein loaded as a function of residence time.

After loading, the column was washed with 10 mM Tris; pH 8.0, for 5 CV at up to 220 cm/hr. The protein of interest was recovered from the resin by elution with 50 mM sodium acetate, pH 3.1 at up to 220 cm/hr. The elution pool yielded greater than 90% recovery of the soluble material in the initial cell broth. The collected protein in the elution pool was stored at 2-8° C. until the next purification step was carried out.

Following the separation, the resin media was cleaned in-place by flowing 5 CV of 6 M Guanidine, pH 8.0 at 220 cm/hr.

The results of this separation demonstrated that a soluble protein expressed in a non-mammalian system can be captured and purified, with high yield, directly from cell lysate broth without having to refold the protein prior to application to a separation matrix.

Example 2

Capture of a Fc-Containing Protein Expressed in a Limited Solubility Form from a Refold Mixture Using Protein A Affinity Chromatography The following experiments demonstrate that an Fc-containing protein can be separated from a refold mixture comprising glycerol, guanidine, urea, and arginine using Protein A affinity media.

In one experiment, a recombinant protein comprising a biologically active peptide linked to the C-terminus of the Fc moiety of an IgG1 molecule via a linker and having a molecular weight of about 57 kDa and comprising 8 disulfide bonds, in a non-mammalian expression system, namely *E. coli*, harvested, refolded under appropriate conditions, and captured using Protein A affinity media.

The growth media in which the cells were growing was centrifuged and the liquid fraction removed, leaving the cells as a paste. The cells were resuspended in water to approximately 60% of the original volume. The cells were lysed by means of three passes through a high pressure homogenizer.

After the cells were lysed, the lysate was centrifuged in a disc-stack centrifuge to collect the protein in the solid fraction, which was expressed in a limited solubility non-native form, namely as inclusion bodies.

The protein slurry was washed multiple times by resuspending the slurry in water to between 50 and 80% of the original fermentation broth volume, mixing, and centrifugation to collect the protein in the solid fraction.

The concentrated protein was then combined in a solubilization solution containing the protein, guanidine, urea, and DTT.

After incubation for one hour, the protein solution was diluted in to a refold buffer containing appropriate levels of arginine, urea, glycerol, cysteine, and cystamine.

In a separate operation, a packed column comprising ProSep VA Ultra™ Protein A affinity resin with dimensions of 1.1 cm internal diameter and ~25 cm height, was prepared and equilibrated with 5 column volumes (CV) of 25 mM Tris, 100 mM sodium chloride; pH 7.4, or similar buffered solution.

An aliquot of a protein comprising an Fc moiety from the refold solution was filtered through a series of depth and/or membrane filter to remove particulates. The conditioned and filtered protein mixture was loaded to approximately 0.35 millimoles total protein/L resin at a 6-10 minute residence time. See FIG. 1, which correlates protein bound and protein loaded as a function of residence time.

After loading, the column was washed with 25 mM Tris, 100 mM sodium chloride; pH 7.4, or similar buffered solution, for 4.5 CV at up to 400 cm/hr. The Fc-contiaing protein was recovered from the resin by elution with 100 mM sodium acetate, pH 3.7 at up to 300 cm/hr. The average level of purity achieved is shown in FIG. 3.

Following the separation, the resin media was cleaned in-place by flowing 5 CV of 150 mM phosphoric acid. The column was regenerated with 5 CV of 50 mM Tris, 10 mM citrate, 6M urea and 50 mM DTT; pH 7.4, washed with water, and then flushed with 3 CV of 150 mM phosphoric acid.

The results of this separation demonstrate that an insoluble protein expressed in a non-mammalian system can be purified directly from a refold buffer without having to dilute the refold buffer prior to application to a separation matrix for more than 150 cycles, as indicated by the table presented in FIG. 3.

In another separation, the Protein A column was cycled with the above procedure 8-10 times and then the final cycle was run as follows: The media was equilibrated with 5 column volumes (CV) of 25 mM Tris, 100 mM sodium chloride; pH 7.4, or similar buffered solution. An aliquot of protein sampled directly from a refold buffer was filtered through a series of depth and/or membrane filter to remove particulates. The conditioned and filtered protein mixture was then loaded on the column to 0.35 millimoles total protein/L resin at a 6-10 minute residence time. See FIG. 1, which correlates protein bound and protein loaded as a function of residence time.

After loading, the column was washed with 25 mM Tris, 100 mM sodium chloride; pH 7.4, or similar buffered solution, for 4.5 CV at up to 400 cm/hr. The protein of interest was recovered from the resin by eluting with 100 mM sodium acetate, pH 3.7 at up to 300 cm/hr. The resin media was cleaned in-place by flowing 5 CV of 150 mM phosphoric acid over it. Finally, the column was flushed with water, regenerated with 5 CV of 50 mM Tris, 10 mM citrate, 6M urea, and 50 mM DTT; pH 7.4, washed with water, and then flushed with 3 CV of 150 mM phosphoric acid. Subsequent analysis of the resin showed no protein carry-over between cycles, demonstrating the ability to re-use the resin after both cleaning methods.

Example 3

Separation of an Fc-Containing Protein from a Refold Mixture Using Cation Exchange Chromatography The following experiments demonstrate that an Fc-containing protein can be separated from a refold mixture comprising glycerol, guanidine, urea, and arginine using cation exchange media.

In one experiment, a recombinant protein comprising a biologically active peptide linked to the C-terminus of the Fc moiety of an IgG1 molecule via a linker and having a molecular weight of about 57 kDa and comprising 8 disulfide bonds, was expressed in a non-mammalian expression system, namely *E. coli*, harvested, refolded under appropriate conditions, and captured using cation exchange media.

The growth media in which the cells were growing was centrifuged and the liquid fraction removed, leaving the cells as a paste. The cells were resuspended in water. The cells were lysed by means of multiple passes through a high pressure homogenizer. After the cells were lysed, the lysate was centrifuged to collect the protein, which was expressed in a limited solubility non-native form, namely as inclusion bodies. The protein slurry was washed multiple times by resuspending the slurry in water, mixing, and centrifugation to collect the protein. The concentrated protein was then transferred to a solubilization buffer containing guanidine and DTT. After incubation for one hour, the protein solution was diluted in to a refold buffer containing appropriate levels of arginine, urea, glycerol, cysteine, and cystamine.

In a separate operation, a packed column comprising EMD Fractogel $SO_3^-$ cation exchange resin with dimensions of 1.1 cm internal diameter and 20 cm height, was prepared and equilibrated with 5 column volumes of 30 mM MES; pH 4.5 buffered solution.

An aliquot of a protein comprising an Fc moiety was sampled directly from a refold solution, was diluted 3-fold with water, titrated with 50% hydrochloric acid to ~pH 4.5 and was filtered through a series of depth and/or membrane filter to remove particulates. The conditioned and filtered protein mixture was loaded to approximately 0.96 millimoles total protein/L resin at 60 cm/hr.

After loading, the column was washed with 30 mM MES; pH 4.5, for 3 CV at 60 cm/hr, then washed with an additional 3 CV of 30 mM MES; pH 6.0. The protein of interest was recovered from the resin by gradient elution over 25 CV between 30 mM MES; pH 6.0 and 30 mM MES, 500 mM NaCl; pH 6.0 at 60 cm/hr. The collected protein in the elution pool was stored at 2-8° C. until the next purification step was carried out.

Purity levels achieved, as determined by SEC and RP-HPLC are shown in FIG. 5.

Following the separation, the resin media was cleaned in-place by flowing 3 CV of 1 M sodium hydroxide, at 120 cm/hr and held for 60 minutes prior an additional 3 CV wash with 1 m sodium hydroxide.

The results of this separation demonstrate that an insoluble protein expressed in a non-mammalian system can be captured and purified from a refold buffer with a variety of separation matrices, including an ion-exchange separation matrix.

Example 4

Re-Usability of Protein A Affinity Resin Used to Isolate a Fc-Containing Protein Directly from a Refold Buffer by Affinity Chromatography In another aspect of the method, a range of column cleaning methods can be employed in conjunction with the methods described herein, allowing the chromatography resins to be reused to an extent that make the method economically feasible. As described in Examples 2 and 3 for the case of Protein A affinity resins, cleaning protocols have been developed and demonstrated to remove product and non-product contaminants from the resin to allow reuse. The cleaning agents include caustic (e.g. sodium or potassium hydroxide), detergents (e.g. SDS or Triton X-100), denaturants (e.g. urea or guanidine-derivatives), and reductants (e.g. DTT, or thioglycolates). These agents can be used in combination or alone.

In order to demonstrate the reusability of column resins following application of the direct capture methods described, an aliquot of pH adjusted and filtered Fc-containing protein was loaded on new, unused resin and resin that had been previously cycled 94 times to evaluate the cleaning of the Protein A resin and the effect on purification binding and separation of an Fc-containing protein with regard to resin history.

The media was equilibrated with 5 column volumes (CV) of 25 mM Tris, 100 mM sodium chloride; pH 7.4, or similar buffered solution. An aliquot of protein sampled directly from a refold buffer was filtered through a series of depth and/or membrane filter to remove particulates. The conditioned and filtered protein mixture was then loaded on the column to approximately 0.35 millimoles total protein/mL resin at a 6-10 minute residence time. See FIG. 1, which correlates protein bound and protein loaded as a function of residence time.

After loading, the column was washed with 25 mM Tris, 100 mM sodium chloride; pH 7.4, or similar buffered solution, for 4.5 CV at up to 400 cm/hr. The protein of interest was recovered from the resin by eluting with 100 mM sodium acetate, pH 3.7 at up to 300 cm/hr. Each column was regenerated using 5 CV phosphoric acid and 5 CV of an acidic buffered solution containing 50 mM Tris, 10 mM citrate, 6M urea, and 50 mM DTT; pH 7.4.

This procedure was repeated for greater than 100 cycles. Selected samples from this reuse study were submitted for SEC-HPLC analysis. The goal was to track the % MP purity, % HMW and % dimer species from the pools as well as to understand the change of purity level from the load. No major differences were observed between the used columns and new columns.

This Example demonstrates that not only can a complex protein be captured from a complex chemical solution, but that the resin can be cycled repeatedly and cleaned and reused reproducibly over a number of industrially-relevant cycles.

What is claimed is:

1. A method of purifying a protein expressed in a non-native soluble form in a non-mammalian expression system comprising:
   (a) lysing a non-mammalian cell in which the protein is expressed in a non-native soluble form to generate a cell lysate;
   (b) contacting the cell lysate with a separation matrix under conditions suitable for the protein to associate with the separation matrix;
   (c) washing the separation matrix; and
   (d) eluting the protein from the separation matrix, wherein the separation matrix is an affinity resin selected from the group consisting of Protein A, Protein G and a synthetic mimetic affinity resin.

2. The method of claim 1, wherein the protein is a complex protein.

3. The method of claim 2, wherein the complex protein is selected from the group consisting of a multimeric protein, an antibody and an Fc fusion protein.

4. The method of claim 1, wherein the non-mammalian expression system comprises bacteria or yeast cells.

5. The method of claim 1, wherein the cell lysate is filtered before it is contacted with the separation matrix.

6. The method of claim 1, further comprising refolding the protein to its native form after it is eluted.

7. A method of purifying a protein expressed in a non-native limited solubility form in a non-mammalian expression system comprising:
   (a) expressing a protein in a non-native limited solubility form in a non-mammalian cell;
   (b) lysing a non-mammalian cell;
   (c) solubilizing the expressed protein in a solubilization solution comprising one or more of the following:
      (i) a denaturant;
      (ii) a reductant; and
      (iii) a surfactant;
   (d) forming a refold solution comprising the solubilization solution and a refold buffer, the refold buffer comprising one or more of the following:
      (i) a denaturant;
      (ii) an aggregation suppressor;
      (iii) a protein stabilizer; and
      (iv) a redox component;
   (e) directly applying the refold solution to a separation matrix under conditions suitable for the protein to associate with the matrix;
   (f) washing the separation matrix; and
   (g) eluting the protein from the separation matrix, wherein the separation matrix is a non-affinity resin selected from the group consisting of ion exchange, mixed mode, and a hydrophobic interaction resin.

8. The method of claim 7, wherein the non-native limited solubility form is a component of an inclusion body.

9. The method of claim 7, wherein the protein is a complex protein.

10. The method of claim 7, wherein the complex protein is selected from the group consisting of a multimeric protein, an antibody, a peptibody, and an Fc fusion protein.

11. The method of claim 7, wherein the non-mammalian expression system is bacteria or yeast cells.

12. The method of claim 7, wherein the denaturant of the solubilization solution or the refold buffer comprises one or more of urea, guanidinium salts, dimethyl urea, methylurea and ethylurea.

13. The method of claim 7, wherein the reductant comprises one or more of cysteine, dithiothreitol (DTT), beta-mercaptoethanol and glutathione.

14. The method of claim 7, wherein the surfactant comprises one or more of sarcosyl and sodium dodecylsulfate.

15. The method of claim 7, wherein the aggregation suppressor is selected from the group consisting of arginine, proline, polyethylene glycols, non-ionic surfactants, ionic surfactants, polyhydric alcohols, glycerol, sucrose, sorbitol, glucose, Tris, sodium sulfate, potassium sulfate and osmolytes.

16. The method of claim 7, wherein the protein stabilizer comprises one or more of arginine, proline, polyethylene glycols, non-ionic surfactants, ionic surfactants, polyhydric alcohols, glycerol, sucrose, sorbitol, glucose, tris, sodium sulfate, potassium sulfate and osmolytes.

17. The method of claim 7, wherein the redox component comprises one or more of glutathione-reduced, glutathione-oxidized, cysteine, cystine, cysteamine, cystamine and beta-mercaptoethanol.

18. The method of claim 1 or 7, further comprising the step of washing the separation matrix with a regeneration reagent.

19. The method of claim 18, wherein the regeneration reagent is one of a strong base or a strong acid.

20. The method of claim 19, wherein the strong acid is phosphoric acid.

21. The method of claim 19, wherein the strong base is sodium hydroxide.

22. The method of claim 18, wherein the regenerating comprises washing the separation matrix with a solution comprising one or both of a chaotrope present at a concentration of 4-6 M and a reductant.

23. The method of claim 22, wherein the chaotrope is one of urea, dimethyl urea, methylurea, ethylurea, and guanidinium.

24. The method of claim 22, wherein the reductant is one of cysteine, dithiothreitol (DTT), beta-mercaptoethanol and glutathione.

25. The method of claim 18, wherein the regenerating comprises washing the separation matrix with a solution comprising 50 mM Tris, 10 mM citrate, 6 M urea, 50 mM dithiothreitol (DTT) at pH 7.4.

* * * * *